United States Patent [19]

Cabrera

[11] Patent Number: 4,507,977
[45] Date of Patent: Apr. 2, 1985

[54] LIQUID METERING AND TRANSFER VALVE ASSEMBLY

[75] Inventor: Pedro P. Cabrera, Miami, Fla.

[73] Assignee: Coulter Electronics, Inc., Hialeah, Fla.

[21] Appl. No.: 502,672

[22] Filed: Jun. 9, 1983

Related U.S. Application Data

[63] Continuation-in-part of Ser. No. 312,218, Oct. 19, 1981, Pat. No. 4,445,391.

[51] Int. Cl.$^3$ .............................................. B01L 3/02
[52] U.S. Cl. .................................. 73/864.12; 422/103
[58] Field of Search ........... 73/863.72, 863.73, 864.81, 73/864.83, 864.84, 864.21

[56] References Cited

U.S. PATENT DOCUMENTS

| | | | |
|---|---|---|---|
| 3,991,055 | 11/1976 | Godin | 73/864.84 |
| 4,152,391 | 5/1979 | Cabrera | 73/864.83 |
| 4,387,076 | 6/1983 | Cabrera et al. | 141/130 |
| 4,445,391 | 5/1984 | Cabrera | 73/864.12 |

Primary Examiner—S. Clement Swisher
Attorney, Agent, or Firm—Silverman, Cass & Singer, Ltd.

[57] ABSTRACT

A liquid diluting valve assembly for delivering a pair of different sample volumes in the microliter range along with a predetermined volume of diluent to different locations. The valve assembly includes a pair of outer discs and an inner disc sandwiched therebetween, the facing surface portions being sealingly frictionally engaged. The discs have central axial passages aligned to accommodate a spindle the inner disc being independently movable relative to the other discs. The discs carry passageways with at least one segmenting passageway provided in the inner disc. One of the outer discs is stationary and carries an external hollow loop having a precise volume in the microliter range. The other outer disc carries a single outwardly extending aspirator probe for introduction of a liquid sample from an exterior sample source, the probe being coupled in series with the external hollow loop.

After a continuous stream of sample is disposed through the serially connected segmenting passageway and loop, the inner member is rotated to place the content of the segmenting passageway in communication with an exterior source of diluent and a passage leading to the exterior of the valve assembly for delivery of the resulting dilution to a selected location. Backwash may be effected by reverse rotation of the inner disc.

10 Claims, 17 Drawing Figures

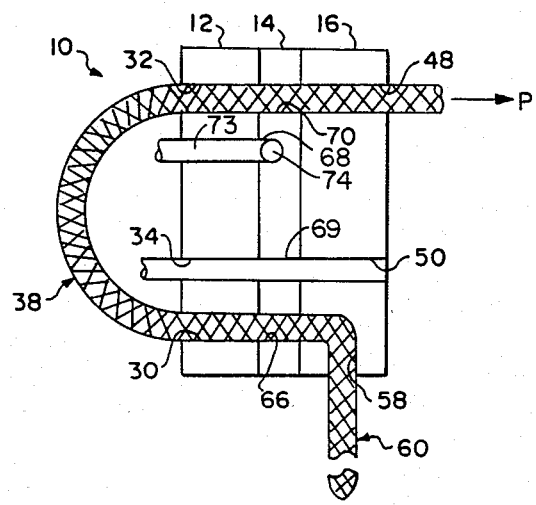
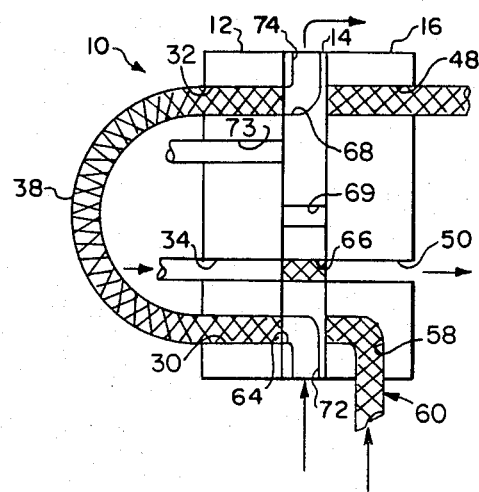
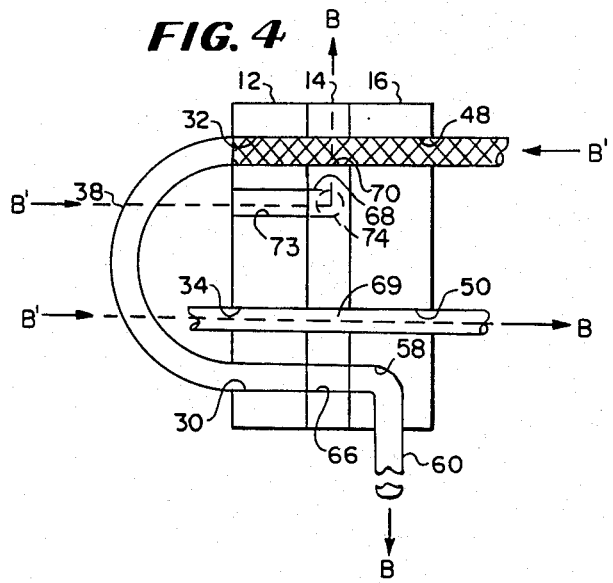

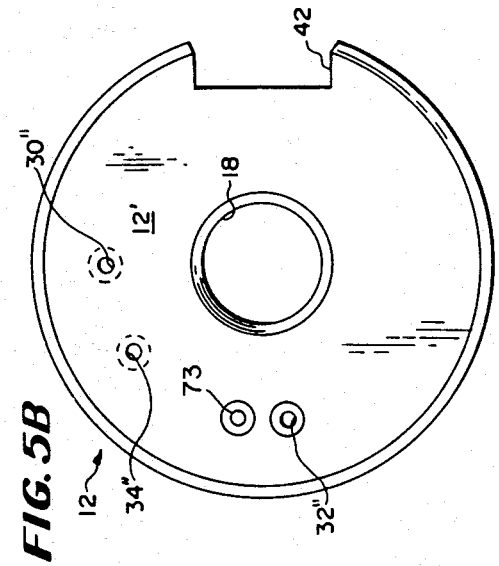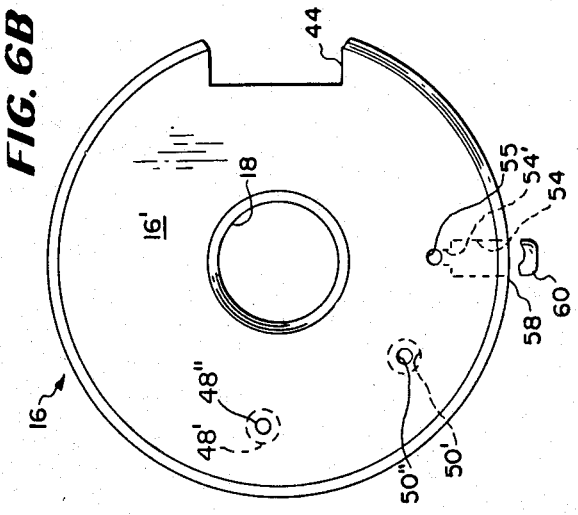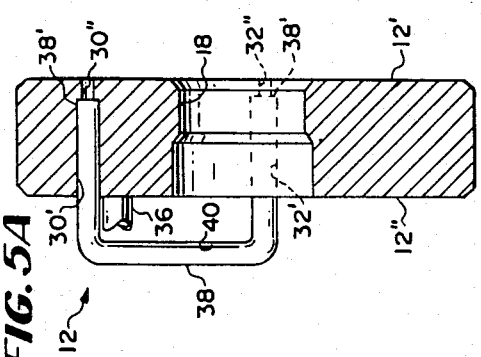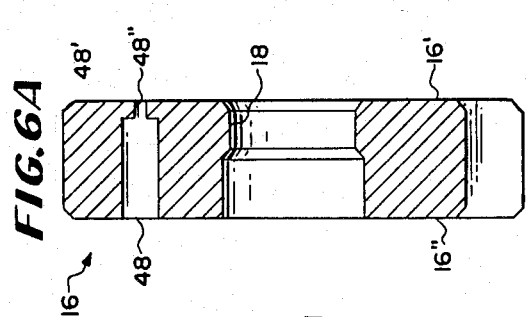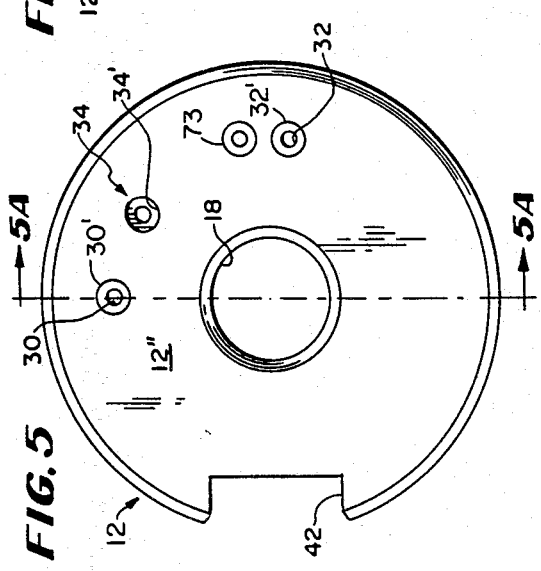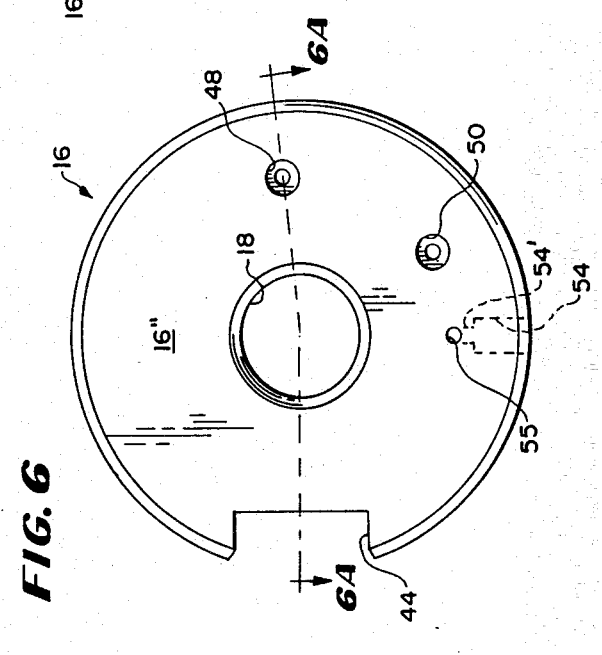

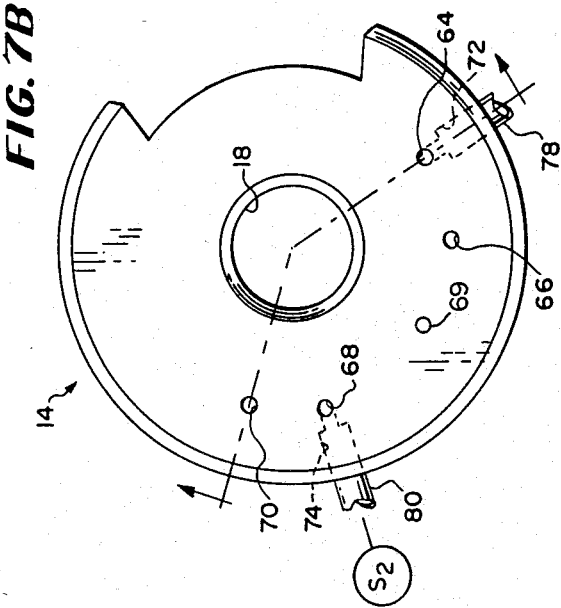
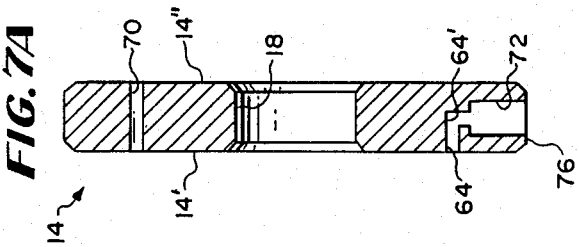
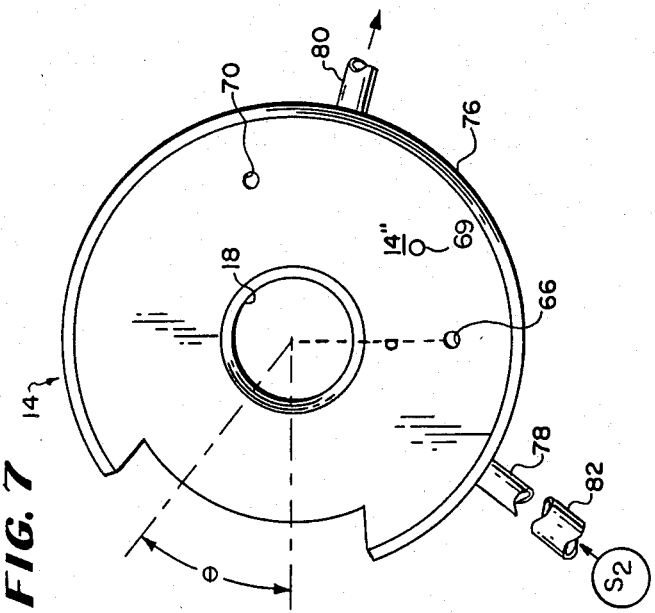

LIQUID METERING AND TRANSFER VALVE ASSEMBLY

CROSS REFERENCE TO RELATED PATENTS AND PATENT APPLICATIONS

This invention is a continuation-in-part of U.S. Ser. No. 312,218 filed Oct. 19, 1981, now U.S. Pat. No. 4,445,391 granted May 1, 1984 and further is an improvement over the liquid transfer valves of the type disclosed in applicant's U.S. Pat. No. 4,152,391 granted on May 1, 1979 and assigned to the Assignee of this application, said patents being hereby incorporated by reference into this application and made a part thereof for description of the background and functional operations of the diluting systems and valve assemblies therein disclosed.

Also hereby incorporated by reference herein and made a part hereof are U.S. Pat. Nos. 3,567,390 3,991,055 and 4,387,076 granted respectively Mar. 2, 1971, Nov. 9, 1976 and June 7, 1983 and also owned by the Assignee of this application.

BACKGROUND OF THE INVENTION

This invention relates generally to liquid transfer systems, and more particularly provides a liquid transfer valve of the rotary operating type for measuring and dispensing precise microliter volumes of samples whereby a pair of measuring chambers is established in a series coupled relationship which is capable of providing simultaneously a pair of precisely measured, different liquid volumes and directing each to a pair of different predetermined locations, each along with a respective known volume of diluent.

Further, the invention includes a rotary valve assembly as described wherein one of the members carries suitable passageways leading to or directly coupled with a pair of angularly spaced probes, one of which involves piercing of an otherwise sealed sample container or source. The probe carrying valve element is independently rotatable to select one or the other of the probes.

The liquid transfer valve provided in the referenced U.S. Pat. No. 4,152,391 is a three part rotary liquid transfer valve assembly which includes an internal segmenting passageway and at least one external hollow loop of precise internal volume thereby to provide the different volumetric quantities of a single liquid sample for dilution, each sample quantity being directed, along with a common volume of diluent, simultaneously to different predetermined locations. The segmenting passageway was provided in a center movable disc of the valve assembly and the external loop was connected directly to said center disc. External connections for feed of diluent and for coupling to lines leading to the predetermined locations were made to the outer portions of the valve which were stationary. This construction required relatively large volumes, especially for the external loop as its length required passage through one of the stationary valve members of the prior valve assembly. This gave rise to considerable so-called dead space whose volume was useless and contributed to considerable waste of sample. In addition to the relatively high cost of manufacture, the complexities of system operation required many connection couplings resulting in possible trouble areas resulting in wear and/or leakage. Considerable demand also has been encountered for conservation of sample volumes required for the testing procedure.

Conventionally, prior valves as used commercially commonly included the feature thereof providing a second external loop also coupled to the center movable disc. The second loop functions as a measuring chamber when a prediluted sample was employed. Accordingly, not one but two external loops were required in the valve assembly to cover the possibility of using a prediluted sample, even if rarely encountered. Clearly this added to the cost. Where prediluted samples were encountered, a section of the transfer valve was not employed and in fact, was blocked off. Nevertheless, this section was required to be provided.

Sample volumes required to make the required dilutions were much higher than the minimums needed to make dilutions required by the technologically improved analytical apparatus now available. The quantities of samples obtained are limited and often are minimal, many times in the microliter range. Smaller volume sample dilutions were capable of being handled successfully. Nevertheless, the structures of the available valve assemblies sharply limited possible reduction in the actual sample volumes required in order to make dilutions for testing.

Thus a need has arisen to provide relatively small precisely measured volumes of liquid sample even in the microliter range, so as to minimize actual raw sampling volume requirements. Fulfillment of such need should be accomplished without increasing the complexity either of fabrication or operation of the transfer valve assembly. Accuracy is paramount. Capability of substitution of the resulting valve assembly for already installed prior valve assemblies, i.e. retro-fit, is an important factor which must be considered in providing for microliter sampling capability. One way of fulfilling the aforesaid need would be to reduce considerably the volume of dead space within any valve assembly employed, but there is considerable difficulty in effecting such reduction with presently available valve assemblies.

A need also has arisen for employing probe meansto pierce a sealed sample source, where, for example, a seal can be provided by a membrane applied sealingly over the top of a sample container. Since versatility is a highly desirable attribute of an analytical system, it would be of considerable advantage to provide a valve assembly having the advantages of the segmenting passageways and external loop with means to accommodate one or the other of the sample sources. This is particularly useful where aspiration of sample into the system is automatically effected, say by piercing of the sealed containers on a sequential somewhat continuous preselected series of containers.

SUMMARY OF THE INVENTION

A rotary operating liquid metering and transfer valve for use in a diluting system, said valve including means defining a pair of measuring chambers arranged in series connection with a source of sample and themselves, one of said chambers constituting an external loop of precise interior volume and the other comprising a segmenting passageway, the loop coupled in series with the segmenting passageway for drawing of a continuous sample therethrough and means isolating each of said pair and respectively coupling each to a different source of diluent and directing the measured sample volumes along with associated diluent to different preselected locations.

The valve assembly comprises a pair of stationary outer disc members and a rotary inner disc sandwiched therebetween and sealingly engaged with the interior faces of both outer discs. The hollow external loop is secured to one of the outer discs. The segmenting passageway is provided in the inner disc and constitutes the first measuring chamber. The loop secured to the outer disc constitutes the second measuring chamber.

The valve assembly operates between two conditions, load and delivery.

An aspirator probe is coupled to the other of the stationary discs, directly or indirectly, and communicates to the serially connected chambers in one condition of the valve for drawing a continuous sampling through both measuring chambers. In one embodiment of the invention the probe carrying disc is rendered independently rotatable relative to the inner disc member and a second aspirator probe coupled thereto angularly disposed relative to the first mentioned aspirator probe. Suitable matching communicating passageways also are provided in the probe-carrying disc to afford communication interior of the valve assembly. The second probe preferably has a piercing tip at its free end or is capable of being coupled to a piercing tip bearing arrangement. The operator can elect between one or the other of the probes by rotating the probe-carrying disc selectively. The valve operates to isolate the contents of each chamber and at that time, independently to couple said measuring chamber to diluent sources during the second, delivery condition of the valve assembly for dispensing of said isolated volumes and the diluent associated therewith to desired locations. The valve assembly is returned to the first condition for backwashing the passageways and measuring chamber.

There is a marked reduction in dead space interior of the valve.

BRIEF DESCRIPTION OF THE DRAWINGS

FIG. 2 is a diagrammatic elevational view of the improved valve assembly illustrating the relationship thereof during the load or aspiration condition;

FIG. 3 is a diagrammatic elevational view of the improved valve assembly illustrating the relationship thereof during the delivery condition;

FIG. 4 is a diagrammatic elevational view of the improved valve assembly illustrating the relationship thereof during the backwash condition thereof securing subsequent to delivery;

FIGS. 5, 5A and 5B respectively illustrate the outer face, and side elevational sectional view taken along lines 5A—5A of FIG. 5 and an inner face view of one of the respective stationary members of the valve assembly according to the invention;

FIGS. 6, 6A and 6B respectively illustrate the outer face, a side elevational sectional view taken along lines 6A—6A of FIG. 6 and the inner face respectively of the other one of the stationary members of the valve assembly according to the invention;

FIGS. 7, 7A and 7B respectively illustrate the one face, a side elevational view taken along lines 7A—7A of FIG. 7, and the opposite face of the center inner movable member, respectively, of the valve assembly according to the invention;

DESCRIPTION OF PREFERRED EMBODIMENTS

The liquid transfer valve assembly contemplated herein is capable of delivering from a single sample at least two different microliter segments, preferably simultaneously, for dilution with predetermined volumes of diluent. Passages are provided for establishing two sets of fluid paths, one set defining paths for traversal by a predetermined volume of diluent, the other set defining a series connection of a pair of precise measuring chambers of different volumes, one of which is provided by a segmenting passageway formed in the inner or movable valve element and the other being provided by an external hollow loop secured fixedly to one of the stationary members. The external loop and the feeder passageways have precise internal dimensions, preferably holding a volume in the microliter range.

Briefly, the improved valve assembly illustrated in FIGS. 1 through 7A and 7B is formed of a pair of members sealingly engaged with an inner movable member sandwiched therebetween. The valve assembly operates between a first condition during which sample is introduced from a source by way of an aspirator probe driven by an aspiration pump and a second or delivery condition. The aspirator probe can be coupled directly or through a conduit system, to a stationary portion of the valve. In the aspirating condition of the valve a continuous path is established between the aspirating probe via a segmenting passageway (constituting a first measuring chamber) and an external loop (constituting a second measuring chamber through a connecting passageway, leading to the aspiration pump.

The valve assembly is operated to place same in the delivery condition, thereby placing the volume segmented from the continuous path by the segmenting passageway into a path established to direct diluent thereto for delivery from the valve to a selected location.

Simultaneously, the volume of sample contained in the second measuring chamber (namely the internal volume of the external loop) is coupled to a path through which diluent is introduced to sweep said volume of sample from the second measuring chamber for delivery to a second preselected location.

Figure 8:
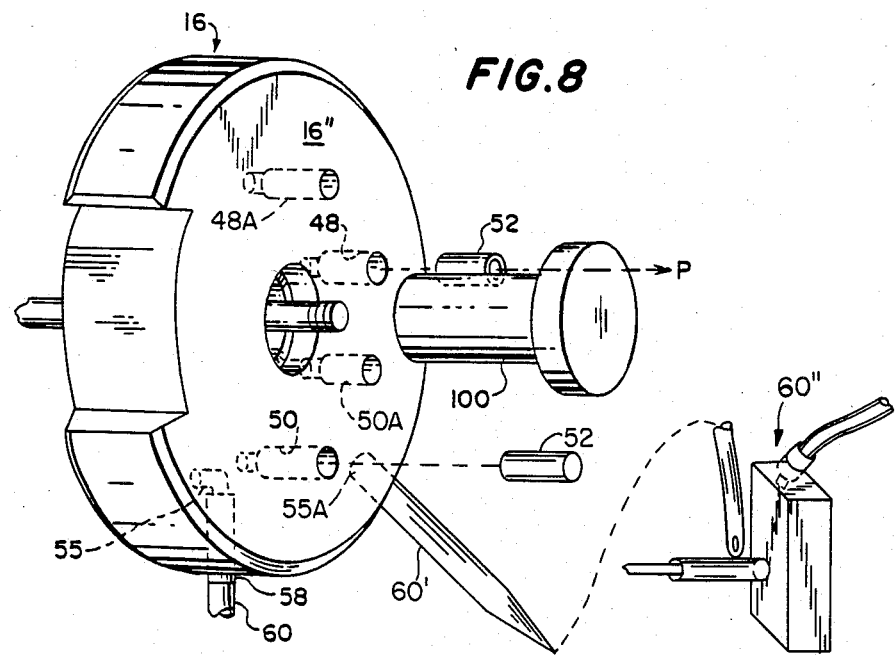
FIG. 8 illustrates one of the outer valve elements of a modified embodiment of the invention.
Figure 9A:
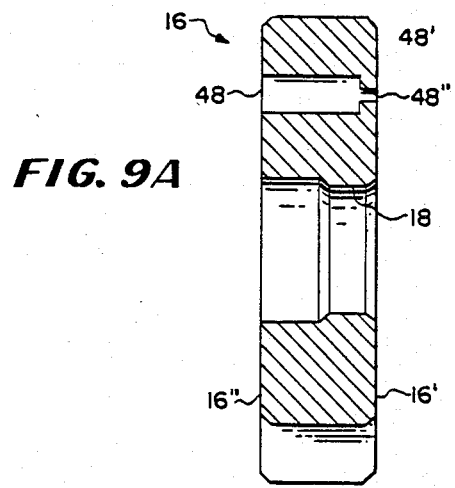
FIGS. 9, 9A and 9B respectively illustrate one face, a side elevational sectional view and the opposite face respectively of the modified outer valve member of FIG. 8.
Figure 9:
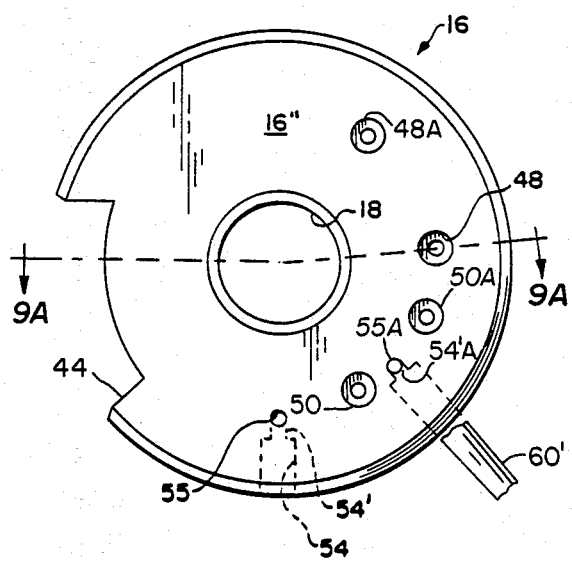
Figure 9B:
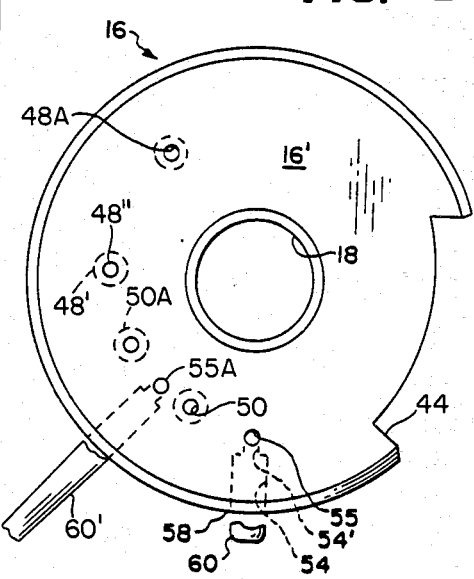

One embodiment of the valve assembly constructed in accordance with the invention as illustrated in FIGS. 1 to 7B inclusive comprises an assembly 10 formed of a pair of coaxially arranged outer stationary disc elements 12 and 16 having a rotatably movable central valve disc element 14 sandwiched therebetween. The stationary elements 12 and 16 are arranged apart only sufficiently to accommodate the thinner central element therebetween. As will be noted in FIGS. 8 through 9B, an embodiment of the invention is illustrated wherein one of the pair of stationary elements is rendered rotatable relative to both the other outer stationary element and the movable inner element.

Figure 1:
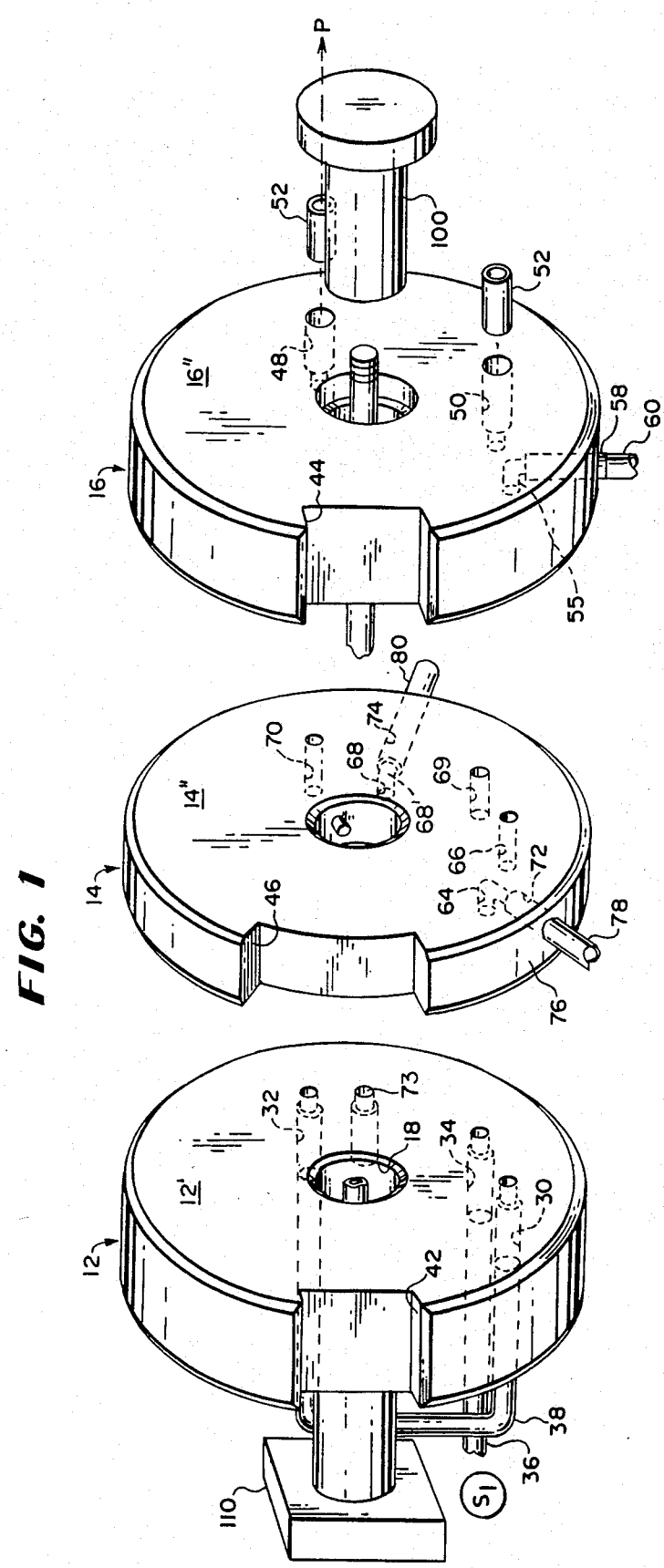
FIG. 1 is an exploded and diagrammatic representation of the liquid transfer valve assembly constructed in accordance with the invention herein.

First referring to FIG. 1, the outer elements 12 and 16 are provided with inner faces 12' and 16' which are engaged sealingly with faces 14' and 14" of the inner element 14. Element 12 also has an outer face 12" and element 16 has outer face 16". Faces 12', 14', 14" and 16' are machined carefully, stress relieved as by heat treatment and coated with an acid resistant chromium oxide-aluminum oxide coating whereby wear is reduced; friction and binding also are reduced.

Each of the valve disc elements 12, 14 and 16 have central passageway 18 of the same inner diameter and all are mounted coaxially on a spindle 20 including support elements 22 and 24 and shaft 26. The mounting is described in U.S. Pat. No. 4,152,391.

In FIG. 1, the left hand element 12 carries the external hollow loop while the right hand element 16 carries either the aspirator probe directly coupled thereto or has the aspirator probe adapted to be coupled thereto by way of a conduit coupling.

A pair of axially parallel through passageways 30 and 32 are formed in stationary outer disc element 12. Another through passageway 34 is formed in disc element 12 parallel axially to the passageways 30 and 32 but angularly spaced therefrom so that a radial line taken through the axial center of passageway 34 defines a precise angle $\theta$ with a radial line taken through the axial center of passageway 30. The passageway 34 includes a short portion 34" of small diameter opening to the inner face 12' while the larger diameter portion 34' opens to the outer face 12" for receiving nipple 36 for coupling to a source of diluent.

The axial centers of passageways 30, 32 and 34 are spaced identically a radial distance "a" from the center axis of the disc 12. Passageways 30 and 32 each have a major portion 30' and 32' of larger diameter compared to the short portions 30" and 32", each of which opens to the inner face 12'. The larger diameter portions 30' and 32' open to the outer face 12" of element 12. (FIG. 5A) Passageway portions 34", 30" and 32" have the same inner diameter.

An external hollow loop 38 is secured to the element 12 with opposite ends 38' seated tightly fully in the larger diameter passageway portions 30' and 32'. The external loop 38 has a precise internal volume. The inner diameter of the hollow loop 38 preferably is uniform with the opposite ends 38' having an inner diameter equal to the diameter of the smaller passageway portions 30" and 32" of passageways 30 and 32. The ends 38' are inserted fully within passageway portions 30' and 32' to about the inner ends of passageway portions 30' and 32'. Thus a precise volume of liquid can be contained within the measuring chamber 40 defined within the hollow external loop.

The stationary valve elements 12 and 16 are provided with circumferential notches 42 and 44 while center valve element 14 is provided with a notch 46 of the same depth but encompassing a greater angular distance along the circumferential opening length than the angular extent of notches 42 and 44. Notches 42 and 44 are aligned with the opposite sides of said notches limiting the relative angular rotation of the center valve element 14 to an angular distance equal to the difference between the length of notches 42, 44 and the length of notch 46. The angular rotation of the center valve element 16 required to change the valve assembly 10 from one condition to its other condition is represented by angle $\theta$.

When the valve elements 12, 14 and 16 are assembled to constitute the valve assembly 10, all of the axially directed passageways and portions thereof which communicate with other passageways carried by the valve elements are coaxial, and all are parallel to the common center axis of said elements 12, 14 and 16.

Valve elements 12, 14 and 16 are mounted coaxially on spindle 110.

A pair of like axially parallel passageways 48 and 50 are formed in the other stationary valve element 16, each passageway 48 and 50 having a larger diameter long portion 48' and 50' opening to the outer face 16" of element 16 with smaller diameter short portion 48" and 50" opening to the inner face 16' of element 16. A cylindrical nipple 52 is tightly seated within each of the large portions 48' and 50' extending outward of element 16 and opening to the exterior of the valve for coupling to the aspirator pump P and to suitable conduits leading to one of the preselected delivery locations, here to the location intended to receive the smaller segmented volume of sample, as will be described.

The stationary valve element 16 also is provided with a radial bore 54 opening to the outer circumferential surface of the element 16. The inner end 54' of bore 54 communicates with a short axial bore 55 formed parallel to the axis of the valve element 16 and opening to the inner face 16' thereof. Thus bores 54 and 55 together constitute an angular passageway 58. The aspirator probe 60 is adapted to be coupled directly to the bore 54 by a conduit, or directly received within bore 54, said bore 54 being of the same inner diameter as passageway portions 30' and 32' and passageway portions 48' and 50' receiving tightly therein, either a nipple 52 or the aspirator probe 60 itself.

The rotatably movable center valve disc element 14 is provided with two pair of passageways, first pair 64 (including bore 74), 66 and second pair 68 (including bore 72), 70. Passageways 66 is formed as a through passageways of precise uniform inner diameter while passageways 64 and 68 extend in an axial direction only partially through the valve element 14 from 14' of said element. The radial bores 72 and 74 are provided in element 14 entering from the outer circumferential surface 76 thereof and communicating to the inner end 64' and 66' of the partial passageways 64 and 68. The inner diameter of bores 72 and 74 is sufficient (the same as the inner diameters of the larger portions of bores 54 and 56, for example, to enable seating therein of nipples 78 and 80, one of which is capable of being coupled to a conduit 82 leading to the preselected delivery location for receiving the larger volume of sample which comprises the interior volume of the hollow loop 38 and the other (80) enabling coupling thereto of a conduit 84 leading from a source S$_2$ of diluent for directing the predetermined volume of diluent to the hollow loop 38 when the valve element 14 is rotated to place the valve 10 in its delivery condition from its load condition. Passageway 70 serves only as a communication channel to the pump, holding its content when rotated for delivery of the measured content of loop 38 and passageways 30, 32.

When the valve element 14 is rotated from its load condition (FIG. 3) to the delivery condition, the through segmenting passageway 66 which defines the smaller measuring chamber is brought into communication with the passageways 34, 50 enabling a predetermined volume of diluent to be directed through the hollow loop 38 and also introduced via passageway 34 to drive the content of the segmenting passageway 66 to the predetermined location via passageway 50 of valve element 16.

The disc 12 is provided with a through passageway 73 which will couple with the bore 74 in number 14, leading out of valve 10 to a location B. Also, the disc 14 has a through passage 69 which, in the backwash position of FIG. 4, will connect with passageways 34 and 50 in the front and rear disc members 12, 16, respectively. Hence, in the backwash (FIG. 4) configuration, rinse fluid can be applied from the left side of the figure into he passageway 73 (as well as into the said passageway 34), which leads into the passageway 69 and then out of the valve 10 selected locations following the paths indicated by B.

FIG. 4 represents the return of the valve 10 to the original aspiration condition but illustrates the backwash mode of operation. The disc 14 has been rotated, after the delivery mode of operation of FIG. 3 has been completed, to place passageway 73 in communication with the passageway defined by bores 68,74 of disc 14. In this condition, the passageway defined by bores 64,73 is placed out of communication with passageway 30. The sample in passageway 66 has been delivered with passageway 66 being returned to communicate to the passageway 58 leading to the probe 60. Passageway 69 is returned to communicate with passageways 34 and 50. Passageway 70, with its isolated content, is returned to communication with passageways 48 and 32. As illustrated in FIG. 4, the rinse liquid is directed from source B$^1$ through the aligned passageways of the valve 10 to locations represented by B. The passageway 69 only is involved in the backwash or rinse mode. Passageway 73 is provided to permit rinse or backwash of the passageway defined by bores 68,74 in element 14. The structure of the valve element 14 herein differs from the similar element 14 of U.S. Pat. No. 4,445,391 (issued out of Ser. No. 312,218 to which reference heretofore was made) by the provision of the additional passageway 69.

As will be observed, the amount of dead space is minimized within the valve assembly 10 as constructed in accordance with the herein invention. Such dead space as remains constitutes only the volume within passageway of the center valve disc 14 and that quantity of volume of sample contained in angular passageway 58 of valve element 16 and in nipple 52 and the conduit leading from nipple 52 to the aspirator pump P. This is minimal compared to prior structures. When delivery is completed simultaneously to the different preselected delivery locations where examination of the respective diluted samples occur, the valve element 14 again is rotated but in the reverse direction to return the valve assembly 10 to its aspiration condition, as illustrated in FIG. 4, but now ready for the rinse or backwash mode. At this time, either the aspirator pump P is reversed to feed diluent from source B$^1$ to the valve 10 or an alternate connection made between a source of diluent and passageway 48 of valve element 16. Diluent is pumped, as from a source thereof, along the same route traversed previously by the sample, i.e. through nipple 52 and passageway 48, through the passageway 70 through the interior of hollow loop 38, through passageway 30, through segmenting passageway 66, then through the angular passageway 58 and traversing the interior of the aspirator probe 60 to a discharge location B.

The internal volume within the external loop 38 is selected to be in the microliter range as compared with the milliliter range. This results in considerable conservation of sample volume required to be obtained.

The valve element of FIGS. 1–7b is substantially the same as illustrated in U.S. Pat. No. 4,445,391 except for the provision of the additional axially parallel passageway 69 and passageway 73 illustrated in FIGS. 8 through 9B and designated generally as valve assembly 10' and the fact that valve element 16' is rotatable between two positions relative to elements 12 and 14 instead of being stationary relative to element 14 of valve 10. Valve element 16' differs from valve element 16 in the provision of two probes 60 and 60' and associated passageways 48A, 55A, 55B and 50A. The disc 16' can be rotated to place one of probes 60 and 60' in the operational path for aspiration. The disc 16' is rotatable in a limited arc and only between the two positions for using probe 60 or probe 60'. The disc 16' is not free wheeling but merely rotates in said limited arc. Probe 60' may be formed with a piercing free end 60'' or may be coupled via a suitable conduit to a needle piercing probe unit displaced from the valve assembly 10' such as disclosed in U.S. Pat. No. 4,387,076. The angular difference between probe 60 and probe 60' in the illustration of the modified valve assembly 10' is 45° so that additional passageways 48A and 50A are formed in disc 16' with additional receiving passages 54A, 55A.

The valve assembly 10' operates in the same manner as assembly 10 except that the operator has the option of using either one of the probes 60 and 60' (or employ a coupling (not shown) conduit to connect probe 60' or equivalent to the needle tip carrying probe assembly 60'').

What I claim is:

1. A liquid metering and transfer valve assembly for use in providing at least a pair of segmented precise samples from a single liquid sample source, the volume of one segmented sample being different than the volume of the other segmented sample of said pair, said valve assembly being operable between a load and a delivery condition and comprising a pair of spaced outer valve elements and a movable inner valve element sandwiched between said outer valve elements, said inner valve element having opposite faces sealingly frictionally engaged with adjacent faces of said outer valve elements, said inner and outer valve elements having first and second segmenting passageway means formed therein for receiving liquid sample therein from a source thereof, the contents of said first and second segmenting passageway means being isolatable one from the other and each respectively combined with a predetermined volume of diluent and delivered with said volume respectively to different preselected exterior locations, at least one of said outer valve elements being stationary, an aspirator probe coupled to the other of said outer valve elements, movement of said inner valve element effecting the segmenting of the liquid sample, the other of said outer valve elements is movable independently relative to the inner valve element and a second aspirator probe is coupled to said other of said outer valve elements spaced angularly from said first aspirator probe, said other of said outer valve elements being selectively movable for placement of one of said first and second aspirator probes in communication with said first and second segmenting passageway means.

2. The valve assembly as claimed in claim 1 in which said first aspirator probe is fixedly secured on said other of the outer valve elements.

3. The valve assembly as claimed in claim 1 in which at least one of said aspirator probes includes a free end having a terminal piercing tip.

4. The valve assembly as claimed in claim 1 and a piercing tip assembly coupled to one of said aspirator probes.

5. The valve assembly as claimed in claim 1 in which said first and second passageway means are in series communication.

6. The valve assembly as claimed in claim 1 wherein said first segmenting passageway means comprises a first segmenting passageway formed in said inner valve element and having a precise internal volume and said second segmenting passageway means comprises an external hollow loop having a precise internal volume different from the volume of the first segmenting passageway.

7. The valve assembly as claimed in claim 1 in which said first segmenting passageway means comprise first and second segmenting portions formed in said inner element and said one of said outer elements carrying an external loop, said inner valve element arranged in the load condition of the valve with said first segmenting portion in communication with one end of said external hollow loop and the second segmenting portion in communication with the opposite end of said external hollow loop, said inner valve element being movable angularly to segment the volume of sample within said first protion isolating same from said continuous volume and placing same in the path taken by the predetermined amount of diluent from said diluent source for delivery to one preselected location, the angular movement isolating the volume within the external hollow loop and placing same in communication with a diluent source for directing said isolated volume together with the diluent to the exterior of said valve assembly for delivery.

8. The valve assembly as claimed in claim 7 in which both of said valve elements are stationary and said aspirator probe element is coupled to the on-loop carrying one of said outer valve elements.

9. A liquid metering and transfer valve assembly for use in a diluting system for providing at least a pair of segmented precise samples from a single liquid sample, the volume of one segmented sample being different than the volume of the other segmented sample of said pair, said valve assembly being operable between a load and a delivery condition and comprising means defining a first and second segmenting portion in series communication for receiving a continuous volume of sample from said source, means for isolating the contents of said first and second segmented portions one from the other and means for combining each of said first and second isolated contents with a precise volume of diluent and delivering said isolated contents with their associated amount of diluent to respectively different preselected exterior locations, said first segmenting portion comprising internal segmenting passageway means having a precise internal volume and said second segmenting portion comprising an external hollow loop having a precise internal volume different from the volume of the segmenting passageway means, said metering and transfer valve assembly having a pair of spaced outer stationary valve elements and an inner movable valve element sandwiched between said outer valve elements, said inner valve element having opposite faces sealingly frictionally engaged with adjacent faces of said outer valve elements, said inner valve element carrying said first segmenting portion and a second segmenting passageway, one of said outer valve elements carrying said external loop, said inner valve element arranged in the load condition of the valve whereat said first segmenting portion is in communication with one end of said external hollow loop and said second segmenting passageway is in communication with the opposite end of said external hollow loop, said inner valve element being movable angularly to segment the volume of sample within said first portion isolating same from said continuous volume and place same in the path taken by the predetermined amount of diluent from said diluent source for delivery to one preselected location, said angular movement isolating the volume within the external hollow loop and placing same in communication with a diluent source for directing said isolated volume together with the associated amount of diluent to the exterior of said valve assembly for delivery to the other preselected location, an angular passageway being formed in the other of said stationary valve elements leading from the outer circumferential surface thereof to the inner face thereof, said angular passageway communicating between the source of sample and the said first segmenting portion in the loading condition of the valve assembly and there is a hollow probe element connected directly to said other of said stationary valve elements at the entrance of said angular passageway, said probe element capable of communicating with a sample source and the other of said stationary valve elements being rendered movable relative to the inner valve element and an additional probe element is secured thereto and additional matching passage means formed in said other valve element for establishing communication to said segmenting portions, said probe carrying valve element capable of being moved to place one or the other of said probes in operational condition.

10. The transfer valve assembly as claimed in claim 9 wherein piercing tip means provided for one or the other of said probes.

* * * * *

UNITED STATES PATENT AND TRADEMARK OFFICE
CERTIFICATE OF CORRECTION

PATENT NO. : 4,507,977
DATED : April 2, 1985
INVENTOR(S) : PEDRO PABLO CABRERA

It is certified that error appears in the above-identified patent and that said Letters Patent are hereby corrected as shown below:

Column 6, line 35, "Passageways" should be --Passageway--;

Column 7, line 9, "he" should be --the--;

Column 7, line 60, after "the" insert --passageways 30, the--;

Column 9, claim 8, "on-loop" should be --non-loop--.

Signed and Sealed this

Eighth Day of April 1986

[SEAL]

Attest:

DONALD J. QUIGG

Attesting Officer

Commissioner of Patents and Trademarks